United States Patent [19]

Yokoyama et al.

[11] Patent Number: 4,526,969
[45] Date of Patent: Jul. 2, 1985

[54] TRIFLUOROMETHYL SUBSTITUTED PERFLUORO QUINOLIZINES

[75] Inventors: Kazumasa Yokoyama, Toyonaka; Chikara Fukaya, Osaka; Yoshio Tsuda, Takarazuka; Taizo Ono, Osaka; Yoshio Arakawa, Suita; Tadakazu Suyama, Kyoto, all of Japan

[73] Assignee: The Green Cross Corporation, Osaka, Japan

[21] Appl. No.: 454,108

[22] Filed: Dec. 28, 1982

[30] Foreign Application Priority Data

Nov. 27, 1981 [JP] Japan ................................. 56-191358

[51] Int. Cl.³ .......................................... C07D 455/02
[52] U.S. Cl. ................. 546/164; 260/245.7; 546/121; 548/453
[58] Field of Search ..................... 546/164; 260/245.7

[56] References Cited

PUBLICATIONS

Plevey et al., J. Fluorine Chem., 21 (1982), pp. 413 et sep., in particular p. 415.
Chambers, "J. Chem. Soc. Perk. Trans. I", pp. 1286–1290, (1972).

Primary Examiner—Glennon H. Hollrah
Assistant Examiner—D. B. Springer
Attorney, Agent, or Firm—Cushman, Darby & Cushman

[57] ABSTRACT

A perfluorobicyclo compound of the general formula:

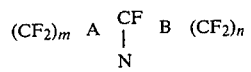

wherein either or both of Ring A and Ring B may optionally be substituted with lower perfluoroalkyl group(s) and m and n each represent 3 or 4.

8 Claims, No Drawings

TRIFLUOROMETHYL SUBSTITUTED PERFLUORO QUINOLIZINES

This invention relates to novel perfluorobicyclo compounds useful as oxygen-carrying components for blood substitutes, oxygen-carrying transfusions, and the like.

More specifically, this invention relates to perfluorobicyclo compounds of the general formula:

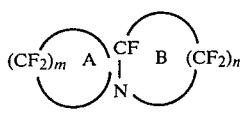

wherein either or both of Ring A and Ring B may optionally be substituted with a lower perfluoroalkyl group(s) and m and n each represent 3 or 4.

In the general formula (I), m and n each represent 3 or 4, and thus Ring A and Ring B each represents a five-membered ring or a six-membered ring, and thus a condensed ring is formed from these two.

Examples of the condensed ring formed by Ring A and Ring B include perfluor oderivatives of perhydroquinolizine, indolizine, pyrrolizine, etc.

Either or both of Ring A and Ring B may optionally be substituted with one or more, preferably b 1–3, lower perfluoroalkyl groups at any position. The perfluoroalkyl group as the substituent is either linear or branched, and examples of these groups include those having 1–4 carbon atoms, such as perfluoromethyl group, perfluoroethyl group, perfluoro-n-propyl group, perfluoro-iso-propyl group, perfluoro-n-butyl group, perfluoro-iso-butyl group, perfluoro-sec-butyl group and perfluoro-tert-butyl group, among which those having 1–3 carbon atoms are preferred. When two or more such substituents are present, they may be different from each other.

The total carbon number in the compound of the general formula (I) is generally 8–12, preferably 9–11, more preferably 10.

The compound of the general formula (I) may be produced by fluorinating a perhydrocompound corresponding to the compound (I). As the fluorination method, there may be mentioned, for example, known fluorination methods such as direct fluorination method, cobalt fluorination method, electrolytic fluorination method, etc.

For the production of the compound (I) of this invention, the electrolytic fluorination method is preferred, and this may be effected by, for example, mixing and dissolving anhydrous hydrogen fluoride and a perhydro compound, as a starting material in an electrolytic cell, and thereafter effecting electrolysis. In said electrolysis, the voltage is generally 3–9 V, the anode current density is generally 1–300 A/dm$^2$, and the bath temperature is generally 4°–10° C.

Since the thus formed compound of the general formula (I) is insoluble in anhydrous hydrofluoric acid, it precipitates in the lower layer of the electrolytic cell.

Separation and purification of the compound (I) from said precipitates may be effected by, for example, adding a liquid mixture of an equal volume of an aqueous alkali solution and an amine compound to the recovered precipitates, separating the lowest layer containing the compound (I) (at that time, partially fluorinated compounds are separated into the amine layer), washing it with an appropriate amount of aqueous acetone containing potassium iodide to remove compounds having fluorine atoms bound to nitrogen atoms, and further subjecting to fractional distillation to separate the compound (I).

Since, in addition to the capability of dissolving large quantities of oxygen, the compound of the general formula (I) of this invention is metabilically inert and also is rapidly eliminated from the body, for example, an aqueous emulsion containing 5–50% (w/v), preferably 10–40% (w/v), of the compound (I) may be prepared and advantageously employed as oxygen-carrying components for blood substituents, oxygen-carrying transfusions, etc. for warm-blooded animals including humans (e.g. dogs, cats, cows, horses, rats, mice, guinea pigs, etc.).

On preparing the aforesaid emulsion, an emulsifier such as polymeric nonionic surfactants, phospholipids, etc., are employed in an amount of 1–5% (w/v) each alone or in combination.

As the medium, a physiologically acceptable aqueous solution is employed, and, if necesary, an isotonizing amount of an isotonizing agent such as glycerol may be added to isotonize the emulsion, and a plasma extender such as hydroxyethylstarch, dextran etc., may be added to adjust the colloid osmotic pressure of the emulsion.

Thus, an aqueous emulsion may be prepared by homogenizing the various components as those described above to a particle size of 0.05–0.3$\mu$, preferably to 0.2$\mu$ or less, using e.g. a high-pressure jet-type homogenizer.

The perhydro compounds corresponding to the compound of the general formula (I), as starting materials are substantially known compounds.

The present invention is further illustrated in more detail below with reference to Examples and Reference Examples, but the invention is not limited thereto.

EXAMPLE 1

As an electrolytic cell, a tank (made of Monel metal (having a capacity of 1.5 l, containing electrodes made of nickel (purity of 99.6% or higher) (6 anodes and 7 cathodes) alternately arranged with an electrode gap of 1.7–2.0 mm with an effective anode surface area of 10.5 dm$^2$ and further equipped with reflex condenser made of copper above the cell, was employed.

Into this electrolytic cell was introduced 1.2 l of anhydrons hydrofluoric acid, and impurities (water and sulfuric acid) present in very small amounts were removed by the preliminary electrolysis. Thereafter, 0.85 mole (130 g) of 4-methyloctahydroquinolizine (4-methylperhydroquinolizine) was dissolved in the hydrofluoric acid, and while passing helium gas at a flow rate of 100 ml/min from the lower part of the cell, the electrolysis was effected with an anode current density of 1.0–2.0 A/dm$^2$, a voltage of 4.0–6.2 V and a bath temperature of 4°–10° C. The electrolysis was continued for 1051 A·hr until the electrolytic voltage reached 9.0 V. Anhydrous hydrofluoric acid was additionally introduced 200 ml per 24 hours. The gas generated during the electrolysis was passed through an iron tube packed with sodium fluoride pellets to remove the entrained anhydrous hydrofluoric acid, an then led into a trap cooled with dry ice-acetone to liquefy and trap the product. On the other hand, the bath liquid in the electrolytic cell separated into two layers, the upper layer containing hydrogen fluoride and the lower layer fluorobicyclo compounds. The lower layer was separated.

The liquid collected by cooling the above generated gas and the lower layer liquid of the electrolytic cell were combined, 70% KOH aqueous solution and diisobutylamine were added in equal volumes, and refluxing was conducted for 7 days. The perfluoro product was separated using a separatory funnel, washed with 70% (w/v) acetone aqueous solution containing 10% (w/v) of potassium iodide, then subjected to fractional distillation using an apparatus for fractional distillation equipped with a spinning band column to obtain perfluoro-4-methyloctahydroquinolizine(perfluoro-4-methylquinolizine) (b.p. 145°–155° C./760 mm Hg). Said compound was confirmed to be the desired compound perfluoro-4-methyloctahydroquinolidine also by the infrared absorption spectrum, F nuclear magnetic resonance spectrum, and mass spectrum.

EXAMPLES 2–101

Perfluorobicyclo compounds corresponding to perhydro compounds used as starting materials were obtained by the procedures similar to those in Example 1. These are sammarized in Table 1.

TABLE 1

| Example No. | Raw material compound | Perfluorocompound | Boiling point (°C./760 mm Hg) |
|---|---|---|---|
| 1 | 4-methylperhydroquinolizine | [structure] | 145–155 |
| 2 | perhydroquinolizine | [structure] | 129–130 |
| 3 | 3-methylperhydroindolizine | [structure] | 125–135 |
| 4 | 2-methylperhydroindolizine | [structure] | 125–136 |
| 5 | 1-methylperhydroindolizine | [structure] | 125–135 |
| 6 | 8a-methylperhydroindolizine | [structure] | 125–136 |
| 7 | 8-methylperhydroindolizine | [structure] | 125–135 |
| 8 | 7-methylperhydroindolizine | [structure] | 125–135 |
| 9 | 5-methylperhydroindolizine | [structure] | 125–135 |
| 10 | 5-methylperhydroindolizine | [structure] | 125–136 |

TABLE 1-continued

| Example No. | Raw material compound | Perfluorocompound | Boiling point (°C./760 mm Hg) |
|---|---|---|---|
| 11 | 3-methylperhydroquinolizine | (perfluoro structure with CF$_3$) | 145–155 |
| 12 | 2-methylperhydroquinolizine | (perfluoro structure with CF$_3$) | 145–155 |
| 13 | 1-methylperhydroquinolizine | (perfluoro structure with CF$_3$) | 145–155 |
| 14 | 9a-methylperhydroquinolizine | (perfluoro structure with CF$_3$) | 145–156 |
| 15 | 3-ethylperhydroindolizine | (perfluoro structure with CF$_2$CF$_3$) | 144–155 |
| 16 | 2-ethylperhydroindolizine | (perfluoro structure with CF$_2$CF$_3$) | 145–155 |
| 17 | 1-ethylperhydroindolizine | (perfluoro structure with CF$_2$CF$_3$) | 145–155 |
| 18 | 8a-ethylperhydroindolizine | (perfluoro structure with CF$_2$CF$_3$) | 145–156 |
| 19 | 8-ethylperhydroindolizine | (perfluoro structure with CF$_2$CF$_3$) | 145–155 |
| 20 | 7-ethylperhydroindolizine | (perfluoro structure with CF$_3$CF$_2$) | 145–155 |
| 21 | 6-ethylperhydroindolizine | (perfluoro structure with CF$_2$CF$_3$) | 145–155 |
| 22 | 5-ethylperhydroindolizine | (perfluoro structure with CF$_2$CF$_3$) | 145–155 |

TABLE 1-continued

| Example No. | Raw material compound | Perfluorocompound | Boiling point (°C./760 mm Hg) |
|---|---|---|---|
| 23 | 2,3-dimethylperhydroindolizine | (structure) | 145–155 |
| 24 | 1,3-dimethylperhydroindolizine | (structure) | 145–156 |
| 25 | 3,8a-dimethylperhydroindolizine | (structure) | 145–155 |
| 26 | 3,8-dimethylperhydroindolizine | (structure) | 145–155 |
| 27 | 3,7-dimethylperhydroindolizine | (structure) | 145–155 |
| 28 | 3,6-dimethylperhydroindolizine | (structure) | 145–155 |
| 29 | 3,5-dimethylperhydroindolizine | (structure) | 145–156 |
| 30 | 1,2-dimethylperhydroindolizine | (structure) | 145–155 |
| 31 | 2,8a-dimethylperhydroindolizine | (structure) | 144–155 |
| 32 | 2,8-dimethylperhydroindolizine | (structure) | 145–156 |

TABLE 1-continued

| Example No. | Raw material compound | Perfluorocompound | Boiling point (°C./760 mm Hg) |
|---|---|---|---|
| 33 | 2,7-dimethylperhydroindolizine | 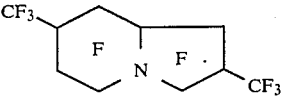 | 145–156 |
| 34 | 2,6-dimethylperhydroindolizine | 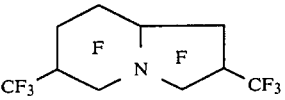 | 144–155 |
| 35 | 2,5-dimethylperhydroindolizine | 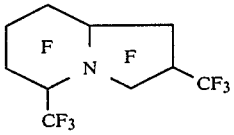 | 145–155 |
| 36 | 1,8a-dimethylperhydroindolizine | 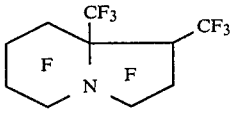 | 145–156 |
| 37 | 1,8-dimethylperhydroindolizine | 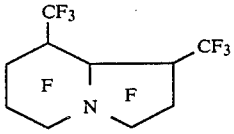 | 145–156 |
| 38 | 1,7-dimethylperhydroindolizine | 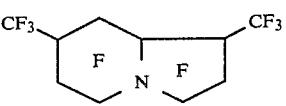 | 145–156 |
| 39 | 1,6-dimethylperhydroindolizine | 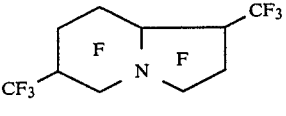 | 144–155 |
| 40 | 1,5-dimethylperhydroindolizine | 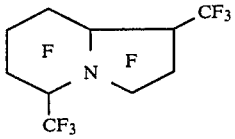 | 145–155 |
| 41 | 8,8a-dimethylperhydroindolizine | 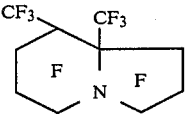 | 145–155 |
| 42 | 7,8a-dimethylperhydroindolizine | 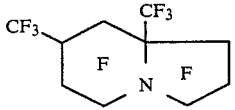 | 145–155 |
| 43 | 6,8a-dimethylperhydroindolizine | 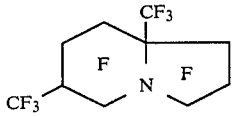 | 145–156 |
| 44 | 5,8a-dimethylperhydroindolizine | 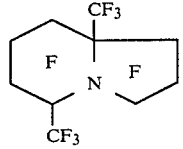 | 145–156 |

TABLE 1-continued

| Example No. | Raw material compound | Perfluorocompound | Boiling point (°C./760 mm Hg) |
|---|---|---|---|
| 45 | 7,8-dimethylperhydroindolizine | 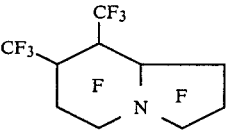 | 145–155 |
| 46 | 6,8-dimethylperhydroindolizine | 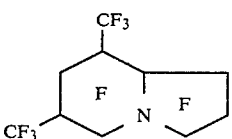 | 145–155 |
| 47 | 5,9-dimethylperhydroindolizine | 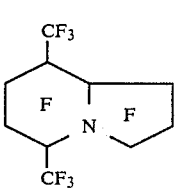 | 145–156 |
| 48 | 6,7-dimethylperhydroindolizine | 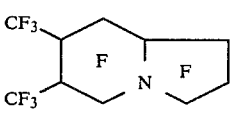 | 145–155 |
| 49 | 5,6-dimethylperhydroindolizine | 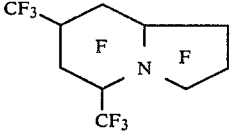 | 145–155 |
| 50 | 5,6-dimethylperhydroindolizine | 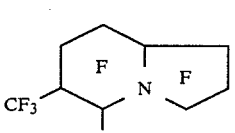 | 145–155 |
| 51 | 3,3-dimethylperhydroindolizine | 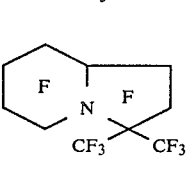 | 145–155 |
| 52 | 1,1-dimethylperhydroindolizine | 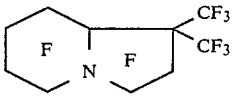 | 145–155 |
| 53 | 8,8-dimethylperhydroindolizine | 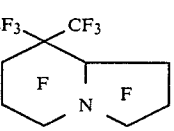 | 145–155 |
| 54 | 7,7-dimethylperhydroindolizine | 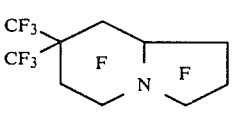 | 145–155 |
| 55 | 6,6-dimethylperhydroindolizine | 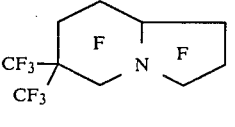 | 145–155 |

TABLE 1-continued

| Example No. | Raw material compound | Perfluorocompound | Boiling point (°C./760 mm Hg) |
|---|---|---|---|
| 56 | 5,5-dimethylperhydroindolizine | (bicyclic structure with N, F substituents and two CF₃ groups) | 145–155 |
| 57 | 3-propylperhydropyrrolizine | (perhydropyrrolizine with F, N, and CF₂CF₂CF₃ substituent) | 145–155 |
| 58 | 2-propylperhydropyrrolizine | (perhydropyrrolizine with CF₂CF₂CF₃, F, N substituents) | 145–156 |
| 59 | 7a-propylperhydropyrrolizine | (perhydropyrrolizine with CF₂CF₂CF₃ at 7a, F, N) | 145–156 |
| 60 | 1-propylperhydropyrrolizine | (perhydropyrrolizine with CF₂CF₂CF₃, F, N) | 145–156 |
| 61 | 3-ethyl-2-methyperhydropyrrolizine | (perhydropyrrolizine with CF₃, F, N, CF₂CF₃) | 145–156 |
| 62 | 3-ethyl-1-methylperhydropyrrolizine | (perhydropyrrolizine with CF₃, F, N, CF₂CF₃) | 145–155 |
| 63 | 3-ethyl-7a-methylperhydropyrrolizine | (perhydropyrrolizine with CF₃ at 7a, F, N, CF₂CF₃) | 145–156 |
| 64 | 3-ethyl-7-methylperhydropyrrolizine | (perhydropyrrolizine with CF₃, F, N, CF₂CF₃) | 145–156 |
| 65 | 3-ethyl-6-methylperhydropyrrolizine | (perhydropyrrolizine with CF₃, F, N, CF₂CF₃) | 145–155 |
| 66 | 3-ethyl-5-methylperhydropyrrolizine | (perhydropyrrolizine with F, N, CF₂CF₃, CF₃) | 145–156 |
| 67 | 2-ethyl-3-methylperhydropyrrolizine | (perhydropyrrolizine with CF₂CF₃, F, N, CF₃) | 145–155 |

TABLE 1-continued

| Example No. | Raw material compound | Perfluorocompound | Boiling point (°C./760 mm Hg) |
|---|---|---|---|
| 68 | 2-ethyl-1-methylperhydropyrrolizine | (structure with CF₃, CF₂CF₃, F, N) | 145–156 |
| 69 | 2-ethyl-7a-methylperhydropyrrolizine | (structure with CF₃, CF₂CF₃, F, N) | 145–156 |
| 70 | 2-ethyl-7-methylperhydropyrrolizine | (structure with CF₃, CF₂CF₃, F, N) | 145–155 |
| 71 | 2-ethyl-6-methylperhydropyrrolizine | (structure with CF₂CF₃, CF₃, F, N) | 145–156 |
| 72 | 2-ethyl-5-methylperhydropyrrolizine | (structure with CF₂CF₃, CF₃, F, N) | 145–156 |
| 73 | 1-ethyl-3-methylperhydropyrrolizine | (structure with CF₂CF₃, CF₃, F, N) | 145–155 |
| 74 | 1-ethyl-2-methylperhydropyrrolizine | (structure with CF₂CF₃, CF₃, F, N) | 145–156 |
| 75 | 1-ethyl-7a-methylperhydropyrrolizine | (structure with CF₃, CF₂CF₃, F, N) | 145–157 |
| 76 | 1-ethyl-7-methylperhydropyrrolizine | (structure with CF₃, CF₂CF₃, F, N) | 145–156 |
| 77 | 1-ethyl-6-methylperhydropyrrolizine | (structure with CF₂CF₃, CF₃, F, N) | 145–155 |
| 78 | 1-ethyl-5-methylperhydropyrrolizine | (structure with CF₂CF₃, CF₃, F, N) | 145–156 |

TABLE 1-continued

| Example No. | Raw material compound | Perfluorocompound | Boiling point (°C./760 mm Hg) |
|---|---|---|---|
| 79 | 7a-ethyl-3-methylperhydropyrrolizine | (structure with CF$_2$CF$_3$, F, N, CF$_3$) | 145–155 |
| 80 | 7a-ethyl-2-methylperhydropyrrolizine | (structure with CF$_2$CF$_3$, F, N, CF$_3$) | 145–156 |
| 81 | 7a-ethyl-1-methylperhydropyrrolizine | (structure with CF$_2$CF$_3$, CF$_3$, F, N) | 145–156 |
| 82 | 1,2,3-trimethylperhydropyrrolizine | (structure with CF$_3$, CF$_3$, F, N, CF$_3$) | 145–155 |
| 83 | 2,3,7a-trimethylperhydropyrrolizine | (structure with CF$_3$, CF$_3$, F, N, CF$_3$) | 145–155 |
| 84 | 2,3,7-trimethylperhydropyrrolizine | (structure with CF$_3$, CF$_3$, F, N, CF$_3$) | 145–155 |
| 85 | 2,3,6-trimethylperhydropyrrolizine | (structure with CF$_3$, F, N, CF$_3$, CF$_3$) | 145–155 |
| 86 | 2,3,5-trimethylperhydropyrrolizine | (structure with CF$_3$, F, N, CF$_3$, CF$_3$) | 145–155 |
| 87 | 1,2,7a-trimethylperhydropyrrolizine | (structure with CF$_3$, CF$_3$, CF$_3$, F, N) | 145–155 |
| 88 | 1,2,7-trimethylperhydropyrrolizine | (structure with CF$_3$, CF$_3$, CF$_3$, F, N) | 145–156 |
| 89 | 1,2,6-trimethylperhydropyrrolizine | (structure with CF$_3$, CF$_3$, F, N, CF$_3$) | 145–156 |

TABLE 1-continued

| Example No. | Raw material compound | Perfluorocompound | Boiling point (°C./760 mm Hg) |
|---|---|---|---|
| 90 | 1,2,5-trimethylperhydropyrrolizine | (structure) | 145-156 |
| 91 | 1,3,7a-trimethylperhydropyrrolizine | (structure) | 144-155 |
| 92 | 1,7,7a-trimethylperhydropyrrolizine | (structure) | 145-156 |
| 93 | 1,6,7a-trimethylperhydropyrrolizine | (structure) | 145-156 |
| 94 | 1,5,7a-trimethylperhydropyrrolizine | (structure) | 144-155 |
| 95 | 3,5,7a-trimethylperhydropyrrolizine | (structure) | 145-156 |
| 96 | 1,3,7-trimethylperhydropyrrolizine | (structure) | 145-156 |
| 97 | 1,3,6-trimethylperhydropyrrolizine | (structure) | 145-156 |
| 98 | 1,3,5-trimethylperhydropyrrolizine | (structure) | 145-155 |
| 99 | 2,6,7a-trimethylperhydropyrrolizine | (structure) | 145-156 |

TABLE 1-continued

| Example No. | Raw material compound | Perfluorocompound | Boiling point (°C./760 mm Hg) |
|---|---|---|---|
| 100 | 2,5,7a-trimethylperhydropyrrolizine | (structure with CF₃ groups) | 145–156 |
| 101 | 4-ethylperhydroquinolizine | (structure with C₂F₅ group) | 165–175 |

REFERENCE EXAMPLE 1

400 g of Vitelline phospholipid was added to 8.5 l of lactic acid added Ringer's solution, and stirred by a mixer to prepare a coarse emulsion, then 2.5 kg of perfluoro-4-methyloctahydroquinolizine was added thereto and stirred vigorously again by the mixer to prepare a coarse emulsion. This coarse emulsion was placed in a liquid tank of a jet emulsifier (manufactured by Manton-Gaulin Co.) and circulated while maintaining the liquid temperature at 50°±5° C. to effect emulsification. The concentration of perfluoro-4-methyloctahydroquinolidine in the obtained emulsion was 27.3% (w/v). The particle diameter as measured by the centrifugal sedimentation method was 0.05–0.25μ. This emulsion was allotted into vials for injection, stoppered and thermally sterilized in a rotary sterilizer, but there was no significant increase in the particle diameter observed.

REFERENCE EXAMPLE 2

An emulsion was obtained by procedures similar to those in Reference Example 1 except that perfluoro-4-methyloctahydroquinolidine was replaced by perpluoro-4-ethyloctahydroquinolidine. The particle diameter of the thus obtained emulsion was 0.0.5–0.25μ.

EXPERIMENTAL EXAMPLE 1

Stability of Emulsions

Water was added to 20 g of each perfluorobicyclo compound selected in the present invention and 4 g of vitelline phospholipid to make the total volume 200 ml, and emulsification was effected using a Manton-Gaulin emulsifier as used above under nitrogen stream at 200–600 kg/cm² while maintaining the liquid temperature at 40°–45° C. Each obtained emulsion was filtered through a 0.65μ membrane filter, allotted into 20 ml-capacity vials, and, after replacing the atmosphere by nitrogen gas, thermally treated at 100° C. for 30 minutes, followed by storing at 4° C. of room temperature to examine the stability. The particle diameter of the emulsion was measured by the centrifugal sedimentation method by Yokoyama et al. [Chem. Pharm. Bull. 22 (12) 2966 (1974)], and from the obtained data, the average particle diameter distribution was calculated using a microcomputer.

Thus, the particle diameter distributions of each perfluoro-carbon emulsion before and after heating, and after heating and storing at 4° C. and room temperature (15°–28° C.) are shown in Tables 2 and 3. As is evident from the results, the emulsions according to the present invention are very stable against heating and the influence on the average particle diameter due to heating was not observed at all. Further, when stored at 4° C. after heating, there was no increase in the average particle diameter observed even after 5 months.

TABLE 2

Stability of Perfluoro-4-methyloctahydroquinolizine Emulsion

|  | Average Particle Diameter, μ | Distribution of Particle Diameter (wt %) | | | |
|---|---|---|---|---|---|
|  |  | <0.1μ | 0.1–0.2μ | 0.2–0.3μ | >0.3μ |
| Before heating | 0.122 | 39.0 | 49.9 | 14.2 | 0.9 |
| Immediately after heating | 0.122 | 35.2 | 56.3 | 8.5 | 0 |
| After 2 weeks |  |  |  |  |  |
| at 4° C. | 0.116 | 37.1 | 59.4 | 3.5 | 0 |
| at R.T.* | 0.127 | 31.2 | 60.1 | 8.7 | 0 |
| After 4 weeks |  |  |  |  |  |
| at 4° C. | 0.122 | 33.0 | 61.5 | 5.5 | 0 |
| at R.T.* | 0.114 | 31.3 | 68.6 | 0.2 | 0 |
| After 5 months |  |  |  |  |  |
| at 4° C. | 0.135 | 25.5 | 64.2 | 10.4 | 0 |

*R.T. = Room Temperature

TABLE 3

Stability of Perfluoro-4-ethyloctahydroquinolizine Emulsion

| | Average Particle Diameter, $\mu$ | Distribution of Particle Diameter (wt %) | | | |
|---|---|---|---|---|---|
| | | <0.1$\mu$ | 0.1–0.2$\mu$ | 0.2–0.3$\mu$ | >0.3$\mu$ |
| Before heating | 0.122 | 38.0 | 51.2 | 10.8 | 0 |
| Immediately after heating | 0.122 | 34.3 | 57.5 | 8.2 | 0 |
| After 2 weeks | | | | | |
| at 4° C. | 0.118 | 37.1 | 61.0 | 1.9 | 0 |
| at R.T.* | 0.128 | 31.3 | 63.5 | 5.2 | 0 |
| After 4 weeks | | | | | |
| at 4° C. | 0.123 | 38.5 | 60.2 | 1.3 | 0 |
| at R.T.* | 0.119 | 34.1 | 60.5 | 5.4 | 0 |
| After 5 months | | | | | |
| at 4° C. | 0.126 | 37.9 | 58.1 | 4.0 | 0 |

*R.T. = Room Temperature

EXPERIMENTAL EXAMPLE 2

Acute Toxicity Test

The acute toxicity test on the preparations of the present invention was carried out using the preparations of the present invention shown in Table 4 which had been physiologically isotonized. The test animals used were Wister-strain male rats (weighing 100–120 g). The emulsion was intravenously administered and the animals were observed for one week after the administration.

The results are such that with either emulsion containing perfluoro-4-methyloctahydroquinolizine or perfluoro-4-ethyloctahydroquinolizine, there was no death case at 100 ml/kg-body weight and thus their toxicity are very small.

TABLE 4

| Composition | | Ratio % (w/v) |
|---|---|---|
| Oil Component (9 vol) | Perfluorobicyclo Compound | 30 |
| | Emulsifying Agent Vitelline Phospholipid | 4.0 |
| Electrolyte (1 vol) | NaCl | 6.00 |
| | NaHCO$_3$ | 2.1 |
| | KCl | 0.336 |
| | MgCl$_2$.6H$_2$O | 0.427 |
| | CaCl$_2$.2H$_2$O | 0.356 |
| | D-Glucose | 1.802 |
| pH | | 8.0 |

EXPERIMENTAL EXAMPLE 3

Distribution of Perfluoro-compound in Organs

Using Wister-strain male rats weighing 120–130 g, the emulsion prepared in Reference Example 1 was administered into the tail vein [at 4 g/kg as perfluoro-4-methyloctahydroquinolidine], and for a period of 3 months after the administration, the content of said compound in the liver, spleen and fat tissues due to uptake were measured by means of gas chromatography.

The content of perfluoro-4-methyloctahydroperhydroquinolizine uptake in each organ 1, 2 and 4 weeks and 3 months after the administration are shown in Table 5. The compound was taken up in greater amounts by the reticulo-endothelial organs shortly after the administration, but soon disappeared rapidly. There was no evidence of adverse influence on the liver or spleen organ.

As a result, the half-life of perfluoro-4-methylperhydroquinolizine was calculated to be 7.33 days.

TABLE 5

| Organ | Time after the administration | Residual Rate of perfluorobicyclo compound, % |
|---|---|---|
| Liver | 1 Week | 19.92 |
| | 2 Weeks | 8.66 |
| | 4 Weeks | 1.88 |
| | 3 Months | 0.30 |
| Spleen | 1 Week | 11.61 |
| | 2 Weeks | 9.33 |
| | 4 Weeks | 2.45 |
| | 3 Months | 0.09 |

EXPERIMENTAL EXAMPLE 4

Anatominal Remarks

Wister-strain male rats weighing 120–130 g were administered with 4 g/kg of the perfluorobicyclo-compound emulsion prepared in Reference Example 1 or 2, and the dissected organs were observed for a period of 3 months after the administration, and further the organs (liver and spleen) were weighed, to determine the weight relatige to the body weight.

One, 2 and 4 weeks and 3 months after the administration of the emulsion, the important organs, i.e. the lung, liver and spleen were observed, to find no evidence of the influence on the organs by either said compound because of their rapid elimination.

What is claimed is:

1. A perfluorobicyclo compound of the general formula:

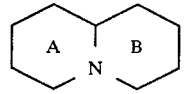

wherein either or both of Ring A and Ring B may optionally be substituted with perfluoroalkyl group(s) having from 1 to 3 carbom atoms, and the total number of carbon atoms in the compound of the above formula is 10 to 12.

2. A compound according to claim 1 which is perfluoro-4-methyloctahydroquinolizine.

3. A compoundd according to claim 1 which is perfluoro-2-methyloctahydroquinolizine.

4. A compound according to claim 1 which is perfluoro-1-methyloctahydroquinolizine.

5. A compound according to claim 1 which is perfluoro-9a-methyloctahydroquinolizine.

6. A compound according to claim 1 which is perfluoro-4-ethyloctahydroquinolizine.

7. A compound according to claim 1 having 10 to 11 carbon atoms.

8. A compound according to claim 1 substantially free from other isomers.

* * * * *